United States Patent
Koh et al.

(10) Patent No.: US 11,280,028 B1
(45) Date of Patent: Mar. 22, 2022

(54) UNBIASED AND SIMULTANEOUS AMPLIFICATION METHOD FOR PREPARING A DOUBLE-STRANDED DNA LIBRARY FROM A SAMPLE OF MORE THAN ONE TYPE OF NUCLEIC ACID

(71) Applicant: **Agency for Science, Technology and Research (A*STAR)**, Singapore (SG)

(72) Inventors: Lian Chye Winston Koh, Singapore (SG); Yiqi Seow, Singapore (SG); Siang Shawn Hoon, Singapore (SG)

(73) Assignee: **AGENCY FOR SCIENCE, TECHNOLOGY AND RESEARCH (A*STAR)**, Singapore (SG)

( * ) Notice: Subject to any disclaimer, the term of this patent is extended or adjusted under 35 U.S.C. 154(b) by 0 days.

(21) Appl. No.: 17/496,796

(22) Filed: Oct. 8, 2021

Related U.S. Application Data

(60) Provisional application No. 63/152,856, filed on Feb. 24, 2021.

(51) Int. Cl.
| | | |
|---|---|---|
| C40B 40/08 | (2006.01) | |
| C12N 15/10 | (2006.01) | |
| C40B 50/06 | (2006.01) | |
| C12Q 1/6876 | (2018.01) | |

(52) U.S. Cl.
CPC .......... *C40B 40/08* (2013.01); *C12N 15/1068* (2013.01); *C12N 15/1093* (2013.01); *C12Q 1/6876* (2013.01); *C40B 50/06* (2013.01); *C12Q 2600/16* (2013.01)

(58) Field of Classification Search
None
See application file for complete search history.

(56) References Cited

U.S. PATENT DOCUMENTS

| | | |
|---|---|---|
| 5,731,171 A | 3/1998 | Bohlander |
| 6,124,120 A | 9/2000 | Lizardi |
| 7,402,386 B2 | 7/2008 | Kurn et al. |
| 7,718,403 B2 | 5/2010 | Kamberov et al. |
| 8,206,913 B1 | 6/2012 | Kamberov et al. |
| 8,481,292 B2 | 7/2013 | Casbon et al. |

(Continued)

FOREIGN PATENT DOCUMENTS

JP  2011500092 A  1/2011

OTHER PUBLICATIONS

Siebert PD et al. "An improved PCR method for walking in uncloned genomic DNA." Nucleic Acids Research, 1995, 23 (6), 1087-1088.

(Continued)

*Primary Examiner* — Kaijiang Zhang
(74) *Attorney, Agent, or Firm* — Idea Intellectual Limited; Margaret A. Burke; Sam T. Yip

(57) ABSTRACT

The present invention relates to an unbiased and simultaneous amplification method for preparing a double-stranded DNA library from a sample of more than one type of nucleic acid. In particular, the present invention provides an unbiased and simultaneous amplification method for preparing a double-stranded DNA library from more than one type of nucleic acid in substantially low amount comparative to non-nucleic acid molecules in the sample within a relatively shorter turnaround time and substantially without any purification step between amplifications and between cDNA preparation and amplification as compared to conventional methods of preparing DNA library.

13 Claims, 8 Drawing Sheets

Specification includes a Sequence Listing.

(56) References Cited

U.S. PATENT DOCUMENTS

| | | | |
|---|---|---|---|
| 8,685,678 | B2 | 4/2014 | Casbon et al. |
| 8,728,766 | B2 | 5/2014 | Casbon et al. |
| 8,741,606 | B2 | 6/2014 | Casbon et al. |
| 9,670,529 | B2 | 6/2017 | Osborne et al. |
| 9,670,536 | B2 | 6/2017 | Casbon et al. |
| 9,920,355 | B2 | 3/2018 | Osborne et al. |
| 10,472,667 | B2 | 11/2019 | Osborne et al. |
| 10,544,446 | B1 | 1/2020 | Tsui et al. |
| 10,626,441 | B2 | 4/2020 | Osborne et al. |
| 10,837,049 | B2 | 11/2020 | Kamberov et al. |
| 2018/0030522 | A1 | 2/2018 | Kamberov et al. |
| 2019/0002958 | A1 | 1/2019 | Cabannes |
| 2019/0271033 | A1 | 9/2019 | Kamberov et al. |

OTHER PUBLICATIONS

Froussard P. rPCR: a powerful tool for random amplification of whole RNA sequences. PCR Methods Appl. Feb. 1993;2(3):185-90.

Gregory R Reyes et al. "Sequence-independent, single-primer amplification (SISPA) of complex DNA populations." Molecular and Cellular Probes, 1991, 5(6), 473-481.

Patrick Froussard et al. "A random-PCR method (rPCR) to construct whole cDNA library from low amounts of RNA." Nucleic Acids Research, 1992, 20(11), 2900.

Mikhail V. Matz et al. "Amplification of cDNA ends based on template-switching effect and step-out PCR." Nucleic Acids Research, 1999, 27(6), 1558-1560.

Santosh Nanda et al. "Universal virus detection by degenerate-oligonucleotide primed polymerase chain reaction of purified viral nucleic acids." Journal of Virological Methods, 2008, 152 (1-2), 18-24.

Javier Alonso Iserte et al. "Family-Specific Degenerate Primer Design: A Tool to Design Consensus Degenerated Oligonucleotides." Biotechnology Research International, 2013, 383646.

Michaela Aubele et al. "Degenerate Oligonucleotide-Primed PCR." Methods in Molecular Biology, 2003, 226, 315-318.

Julio Levano Garcia et al. "Mapping transposon insertion sites by touchdown PCR and hybrid degenerate primers." BioTechniques, 2005, 38(2), 225-229.

Juliana L.R. Fietto et al. "Use of Degenerate Primers and Touchdown PCR for Construction of cDNA Libraries." BioTechniques, 2002, 32, 1404-1411.

Jonas Binladen et al. "The Use of Coded PCR Primers Enables High-Throughput Sequencing of Multiple Homolog Amplification Products by 454 Parallel Sequencing." PLoS ONE, 2007, 2, e197.

Agnieszka Janiak et al. "Application of degenerate oligonucleotide primed PCR (DOP-PCR) for SNP discovery in soybean." Euphytica, 2008, 162, pp. 249-256.

Konstantin A. Blagodatskikh et al. "Improved DOP-PCR (iDOP-PCR): A robust and simple WGA method for efficient amplification of low copy number genomic DNA." PLoS ONE, 12(9), e0184507.

Nona Arneson et al. "Whole-genome amplification by degenerate oligonucleotide primed PCR (DOP-PCR)." Cold Spring Harbor Protocols, 2008, 1, 1-5.

Erin K. Hanson et al. "Whole genome amplification strategy for forensic genetic analysis using single or few cell equivalents of genomic DNA." Analytical Biochemistry, 2005, 346(2), 246-57.

Tomohiko Harada et al. "Evaluation of the Reliability of Chromosomal Imbalances Detected by Combined Use of Universal DNA Amplification and Comparative Genomic Hybridization." Cancer Science, 2000, 91(11), 1119-1125.

Liliana Z. Feher et al. "Improved DOP-PCR-Based Representational Whole-Genome Amplification Using Quantitative Real-Time PCR." Diagn Mol Pathol, 2006, 15(1), 43-48.

Wen-Ho Yang et al. "Methylation profiling using degenerated oligonucleotide primer-PCR specific for genome-wide amplification of bisulfite-modified DNA." Analytical Biochemistry, 2007, 369(1), 120-127.

Angie Ambers et al. "Modified DOP-PCR for improved STR typing of degraded DNA from human skeletal remains and bloodstains." Legal Medicine, 2016, 18, 7-12.

Marine Guillaud-Bataille et al. "Detecting single DNA copy number variations in complex genomes using one nanogram of starting DNA and BAC-array CGH." Nucleic Acids Research, 2004, 32(13), e112.

Michelle Desiree Bonnette et al. "deDegenerate Oligonucleotide Primed-PCR for Multilocus, Genome-wide Analysis From Limited Quantities of DNA." Diagnostic molecular pathology: the American journal of surgical pathology, part B, 2009, 18(3), 165-175.

Simon Hughes et al. "Use of whole genome amplification and comparative genomic hybridisation to detect chromosomal copy number alterations in cell line material and tumour tissue." Cytogenetic and Genome Research, 2004,105(1), 18-24.

Zbigniew T. Czyz et al. "Principles of Whole-Genome Amplification." Methods in molecular biology, 2015, 1347, 1-14.

Martina Höckner et al. "Whole Genome Amplification from Microdissected Chromosomes." Cytogenetic and Genome Research, 2009, 125(2), 98-102.

Jennifer F. Holbrook et al. "Exploring Whole Genome Amplification as a DNA Recovery Tool for Molecular Genetic Studies." Journal of biomolecular techniques: JBT, 2005, 16(2), 125-133.

Alignment search results of SRQ ID Nos. 1,2, and 4-13 on Nucleotide sequences derived from the Patent division of GenBank.

SEQUENCE LISTING

<160> NUMBER OF SEQ ID NOS: 15

<210> SEQ ID NO 1
<211> LENGTH: 27
<212> TYPE: DNA
<213> ORGANISM: Artificial Sequence
<220> FEATURE:
<223> OTHER INFORMATION: Synthesized in the lab

<400> SEQUENCE: 1
cagactacca tgacctgagt cbbbbbb                                        27

<210> SEQ ID NO 2
<211> LENGTH: 38
<212> TYPE: DNA
<213> ORGANISM: Artificial Sequence
<220> FEATURE:
<223> OTHER INFORMATION: Synthesized in the lab
<220> FEATURE:
<221> NAME/KEY: misc_feature
<222> LOCATION: (38)..(38)
<223> OTHER INFORMATION: where "N" represents any of A, T, C or G

<400> SEQUENCE: 2
cagactacca tgacctgagt cttttttttt tttttttvn                                   38

<210> SEQ ID NO 3
<211> LENGTH: 29
<212> TYPE: DNA
<213> ORGANISM: Artificial Sequence
<220> FEATURE:
<223> OTHER INFORMATION: Synthesized in the lab

<400> SEQUENCE: 3
gtcagagtcg aatgcgtact gbbbbbbbb                                              29

<210> SEQ ID NO 4
<211> LENGTH: 21
<212> TYPE: DNA
<213> ORGANISM: Artificial Sequence
<220> FEATURE:
<223> OTHER INFORMATION: Synthesized in the lab

<400> SEQUENCE: 4
cagactacca tgacctgagt c                                                      21

<210> SEQ ID NO 5
<211> LENGTH: 21
<212> TYPE: DNA
<213> ORGANISM: Artificial Sequence
<220> FEATURE:
<223> OTHER INFORMATION: Synthesized in the lab

<400> SEQUENCE: 5
gtcagagtcg aatgcgtact g                                                      21

<210> SEQ ID NO 6
<211> LENGTH: 19
<212> TYPE: DNA
<213> ORGANISM: Artificial Sequence
<220> FEATURE:
<223> OTHER INFORMATION: Synthesized in the lab

<400> SEQUENCE: 6
agatgtgtat aagagacag                                                         19

<210> SEQ ID NO 7
<211> LENGTH: 23
<212> TYPE: DNA
<213> ORGANISM: Artificial Sequence
<220> FEATURE:
<223> OTHER INFORMATION: Synthesized in the lab
<220> FEATURE:
<221> NAME/KEY: misc_feature
<222> LOCATION: (1)..(4)
<223> OTHER INFORMATION: where "N" represents any of A, T, C or G

<400> SEQUENCE: 7
nnnnctgtct cttatacaca tct                                                    23

<210> SEQ ID NO 8
<211> LENGTH: 33
<212> TYPE: DNA
<213> ORGANISM: Artificial Sequence
<220> FEATURE:
<223> OTHER INFORMATION: Synthesized in the lab

<400> SEQUENCE: 8
tcgtcggcag cgtcagatgt gtataagaga cag                                         33

```
<210> SEQ ID NO 9
<211> LENGTH: 34
<212> TYPE: DNA
<213> ORGANISM: Artificial Sequence
<220> FEATURE:
<223> OTHER INFORMATION: Synthesized in the lab

<400> SEQUENCE: 9
gtctcgtggg ctcggagatg tgtataagag acag                          34

<210> SEQ ID NO 10
<211> LENGTH: 27
<212> TYPE: DNA
<213> ORGANISM: Artificial Sequence
<220> FEATURE:
<223> OTHER INFORMATION: Synthesized in the lab
<220> FEATURE:
<221> NAME/KEY: misc_feature
<222> LOCATION: (22)..(27)
<223> OTHER INFORMATION: where "N" represents any of A, T, C or G

<400> SEQUENCE: 10
cagactacca tgacctgagt cnnnnnn                                  27

<210> SEQ ID NO 11
<211> LENGTH: 27
<212> TYPE: DNA
<213> ORGANISM: Artificial Sequence
<220> FEATURE:
<223> OTHER INFORMATION: Synthesized in the lab

<400> SEQUENCE: 11
cagactacca tgacctgagt cdddddd                                  27

<210> SEQ ID NO 12
<211> LENGTH: 27
<212> TYPE: DNA
<213> ORGANISM: Artificial Sequence
<220> FEATURE:
<223> OTHER INFORMATION: Synthesized in the lab

<400> SEQUENCE: 12
cagactacca tgacctgagt chhhhhh                                  27

<210> SEQ ID NO 13
<211> LENGTH: 29
<212> TYPE: DNA
<213> ORGANISM: Artificial Sequence
<220> FEATURE:
<223> OTHER INFORMATION: Synthesized in the lab
<220> FEATURE:
<221> NAME/KEY: misc_feature
<222> LOCATION: (22)..(29)
<223> OTHER INFORMATION: where "N" represents any of A, T, C or G

<400> SEQUENCE: 13
gtcagagtcg aatgcgtact gnnnnnnnn                                29

<210> SEQ ID NO 14
<211> LENGTH: 29
<212> TYPE: DNA
<213> ORGANISM: Artificial Sequence
<220> FEATURE:
<223> OTHER INFORMATION: Synthesized in the lab

<400> SEQUENCE: 14
gtcagagtcg aatgcgtact gdddddddd                                29
```

```
<210> SEQ ID NO 15
<211> LENGTH: 29
<212> TYPE: DNA
<213> ORGANISM: Artificial Sequence
<220> FEATURE:
<223> OTHER INFORMATION: Synthesized in the lab

<400> SEQUENCE: 15
gtcagagtcg aatgcgtact ghhhhhhhh                                        29
```

UNBIASED AND SIMULTANEOUS AMPLIFICATION METHOD FOR PREPARING A DOUBLE-STRANDED DNA LIBRARY FROM A SAMPLE OF MORE THAN ONE TYPE OF NUCLEIC ACID

CROSS-REFERENCE TO RELATED APPLICATIONS

This application claims priority from the U.S. provisional patent application Ser. No. 63/152,856 filed Feb. 24, 2021, and the disclosure of which is incorporated herein by reference in its entirety.

TECHNICAL FIELD

The present invention relates to an unbiased and simultaneous amplification method for preparing a double-stranded DNA library from a sample of more than one type of nucleic acid. In particular, the present invention provides an unbiased and simultaneous amplification method for preparing a double-stranded DNA library from more than one type of nucleic acid in substantially low amount comparative to non-nucleic acid molecules in the sample.

BACKGROUND

Preparation of libraries for high throughput sequencing from a biological or medical samples is not always easy because they are usually significantly low in the amount of nucleic acids. Many conventional methods, in order to cope with this limitation, may require more complex procedure which is more time-consuming and costly, or limited to certain kind of nucleic acid sample, or may lose or add some elements that do not belong to the original sample, implying that there is no simultaneous amplification of the nucleic acid sample in place which avoids or lowers bias between different types of nucleic acids for the same target, especially when the amount of the nucleic acid sample is only up to picogram level.

U.S. Pat. No. 5,731,171 (Bohlander et al.) provided a sequence-independent amplification (SIA), PCR-based method capable of amplifying DNA from minute amounts such as from microdissected chromosomal material. The method involves an initial primer composed of 4-8 random nucleotides, at 3' end and 10-30 nucleotides of defined (non-random) sequence at 5' end, where the random nucleotide can be any of G/A/T/C (in any order). The 3' end of the initial primer should be complementary to random sites throughout the target DNA segments while the defined sequence should constitute a PCR primer which do not form self-homologies, no runs of the same nucleotide, and no overly rich G:C or A:T rich.

U.S. Pat. No. 6,124,120 (Lizardi et al.) provided a non-PCR-based method of multiple strand displacement amplification (MDA) using two set of primers complementary to a pair of double-stranded DNA, where some intervening primers are displaced during replication by the polymerase. Another embodiment of this patent also uses a random set of primers to sequence whole genome. A highly processive polymerase is used in the replication such that overlapping copies of the entire genome can be synthesized in a short time.

However, both Bohlander et al. and Lizardi et al. could not be used to amplify samples with a mix of different nucleic acids including deoxyribonucleic acid (DNA), ribo- nucleic acid (RNA), or any analogues thereof, which is/are either single-stranded or double-stranded, or both, simultaneously without bias.

U.S. Pat. No. 7,402,386 (Kum et al.) disclosed using a RNA-DNA composite primer and DNA- and RNA-dependent DNA polymerases for globally amplifying DNA/RNA polynucleotide targets. The method involved cleavage of RNA portion from RNA/DNA heteroduplex before subsequent amplification.

U.S. Pat. Nos. 7,718,403 and 8,206,913 (Kamberov et al.) disclosed methods for whole genome amplification (WGA) and whole transcriptome amplification (WTA) including a library generation step and a library amplification step, which involve the use of random primer and specific DNA polymerase in the library generation step to generate the first strand from the DNA/RNA template, where the variable region of the primer comprises at most 3 random nucleotides each composed of two non-complementary nucleotides such that primers will not self-hybridize or cross-hybridize with each other. Choosing random nucleotides composed of two non-complementary nucleotide bases instead of random nucleotides composed of at least three non-complementary nucleotide bases does not effectively reduce cross-hybridization among the pool of random primers if there are only at most 3 random nucleotides in each of the random primer because PCR favors generation of short amplicons. It is important to reduce the ability to form non-specific amplicons in order to prevent sequestration of polymerase towards unproductive amplicons.

U.S. Pat. No. 8,741,606 (Casbon et al.) disclosed a method of tagging degenerate base region (DBR) to a nucleic acid molecule on both ends to be sequenced to result in an asymmetrically tagged nucleic acid molecule because two different DBRs. The DBRs include a sequencing primer site for subsequent PCR. In certain embodiments of '606, DBR may be 3 to 10 random nucleotides-long, and each DBR may have different base composition such as 4-base DBR may have any of the following compositions: NNNN; NRSN; SWSW; BDHV (according to IUPAC nucleotide code). '606 involves addition of two different DBRs on both ends of the nucleic acid molecule to be sequenced, and some functional domains such as sequencing primer site and unique multiplex identifier for sequencing purpose, but it was not primarily designed for library preparation from a mix of different nucleic acids including both DNA and RNA in either single-stranded or double-stranded form.

U.S. Pat. No. 8,728,766 (Casbon et al.) disclosed a method for processing a genomic DNA sample including using a population of first primers to hybridize a genomic sample of initial target DNA molecules, where the first primers include different DBR sequences 5' to a target-specific sequence, and different DBR sequences include at least one of R, Y, S, W, K, M, B, D, H, V, N according to IUPAC nucleotide code, or their modified versions. In certain examples, RYB serves as DBR sequence while DHVB serves as target-specific sequence. In those example, the total number of different sequences from those random nucleotides could be 972 (2×2×3×3×3×3×3). There were still only three random nucleotides in the DBR sequence employed in the first primers of '766. Cross-hybridization among primers could still happen under suitable conditions.

U.S. Pat. No. 9,920,355 (Osborne et al.) provided a method of library preparation comprising including deoxymethyl-cytidine triphosphate in different concentrations in the RT reaction mix for first strand, second strand generations, and/or PCR amplifications to facilitate fragmentation using a specific restriction enzyme digestion.

Therefore, a one-pot method for preparing a DNA library from a sample in substantially low amount of a mixture of different types of nucleic acids without bias is needed for high throughput sequencing. By using a set of carefully designed DNA strand generation primers to target a pool of nucleotide sequences, notwithstanding any forms of nucleic acid samples, library preparation can be generated from a sample of a mix of different forms of nucleic acids simultaneously without bias, i.e., a one-pot synthesis method, while self-priming is efficiently avoided during the DNA strand generation from the nucleic acid samples.

SUMMARY OF INVENTION

Accordingly, in a first aspect of the present invention, there is provided an unbiased and simultaneous amplification method for preparing a library from a sample of more than one type of nucleic acid in substantially low amount comparative to non-nucleic acid molecules, where the method includes:

providing the sample of more than one type of nucleic acid including single-stranded and/or double-stranded DNA and/or RNA as a template of subsequent extensions and amplifications;

preparing a first DNA strand from said sample including annealing one or more first DNA strand generation primers to any of the DNA and/or RNA template, and extending from the annealed first DNA strand generation primer including employing a DNA polymerase that enables a one-pot synthesis of the first DNA strand from either or both of DNA and/or RNA templates to obtain the first DNA strand, wherein each of the first DNA strand generation primers includes:

a first nucleotide sequence that includes a constant adaptor sequence on the 5' end followed by a poly-thymidine sequence and two random nucleotides, said poly-thymidine sequence including at least ten thymidine bases followed by a random nucleotide selected from a set of adenine cytosine or guanine and further followed by a random nucleotide selected from a set of four bases of adenine, cytosine, guanine and thymidine, and a second nucleotide sequence that includes a constant adaptor sequence on the 5' end followed by five, six or seven random nucleotides, more preferably six repeating random nucleotides, said random nucleotide being a nucleotide base randomly selected from a set of any three bases of adenine, cytosine, guanine and thymidine, or a combination thereof preparing a second strand of DNA or DNA fragment including annealing a second DNA strand generation primer to the first DNA strand after dissociation from the DNA and/or RNA template and denaturing thereof, and extending from the annealed second DNA strand generation primer including employing a DNA polymerase having strand displacement activity, wherein said second DNA strand generation primer includes:

a random nucleotide sequence including a plurality of said random nucleotides at 3'-end of the second strand of DNA, and a second adaptor sequence at 5'-end thereof that is physically linked to the random nucleotide sequence, wherein the plurality of said random nucleotides includes at least eight random nucleotides, more preferably eight repeating random nucleotides, wherein each of said at least eight random nucleotides is selected from a set of any three bases of adenine, cytosine, guanine and thymidine;

amplifying the second strand of DNA or DNA fragment via a polymerase chain reaction including annealing a pair of amplification primers including the first adaptor sequence at 5'-end in one of the amplification primers and the second adaptor sequence at 5'-end in another one of the amplification primers to the second strand of DNA or DNA fragment to obtain a plurality of amplicons such that each of the amplicons includes at least the first and second adaptor sequences, wherein each of the first and second adaptor sequences has at least one nucleotide modified by methylation;

fragmenting the amplicons into a plurality of double-stranded DNA fragments including reacting the amplicons with a methylation-specific restriction enzyme in order to obtain the double-stranded DNA fragments absent the first and second adaptor sequences.

In one embodiment, the random nucleotide is selected from a set of cytosine, guanine and thymidine, a set of adenine, guanine and thymidine, a set of adenine, cytosine and thymidine, a set of adenine, cytosine and guanine, or a set of adenine, guanine, cytosine and thymidine.

In another specific embodiment, each of the random nucleotides in the first strand generation primers is jointly or independently selected from B, D, H, or V according to IUPAC nucleotide code.

In yet another specific embodiment, each of the random nucleotides in the second strand generation primers is jointly or independently selected from B, D, H, or V according to IUPAC nucleotide code.

In a more specific embodiment, the random nucleotide sequence of the first strand generation primers and/or second strand generation primers includes six to eight random nucleotides where the last random nucleotide may be different from the rest of the random nucleotides in the random nucleotide sequence according to IUPAC nucleotide code.

In another more specific embodiment, the random nucleotide sequence of the first strand generation primers and/or second strand generation primers includes six to eight random nucleotides where except the last random nucleotide, the rest of the random nucleotides in the random nucleotide sequence are jointly selected from one of the random nucleotides with random selection of three out of four nucleotide bases according to the IUPAC nucleotide code.

In another embodiment, a methylated nucleoside triphosphate is added into a reaction mixture of the first and/or second DNA strand or DNA fragment preparation(s) and/or the polymerase chain reaction.

In a preferred embodiment, wherein the methylated nucleoside triphosphate is deoxy-methyl-cytidine triphosphate in a concentration of 0.01% to 25% to result in 0.01 to 25% of cytosines in the product being methylated after the polymerase chain reaction.

In other embodiment, one cytosine in each of the first and second adaptor sequences is modified by methylation to become methyl-cytosine in the amplification primers in order to obtain a plurality of amplicons with methylated nucleotide bases.

In yet another embodiment, the present method further includes appending at least a pair of double-stranded adaptors, wherein one strand thereof comprises a 4-random nucleotide overhang complementary to a 4-nucleotide overhang on both ends of the double-strand DNA fragments after said fragmenting in order to obtain double-stranded DNA fragments under 1000 nucleotide in size containing the double-stranded adaptors appended on both ends thereof.

In a further embodiment, the double-stranded DNA fragments having been appended with the corresponding double-stranded adaptors can be further appended with a pair of sequencing adaptors on both ends thereof for an optional subsequent barcoding.

In another embodiment, the double-stranded DNA fragments having been appended with the corresponding double-stranded adaptors are amplified by annealing a pair of primers to generate more amplicons thereof before appending a pair of sequencing adaptors if subsequent barcoding is intended.

A second aspect of the present invention relates to a kit for generating a library according to the method described herein. The kit includes a substrate conjugated with two of the first strand generation primers for annealing RNA template include single-stranded RNA template and single-stranded mRNA. The kit also includes reverse transcriptase, an RNAse, and reaction mixture for initiating reverse transcription of the first DNA strand from the annealed first strand generation primers. The kit further includes the second strand generation primer, a polymerase with strand displacement activity, and reaction mixture for polymerization of the second DNA strand from the first DNA strand after separating the substrate from the liquid after the reverse transcription. The kit additionally includes amplification primers, enzyme and reaction mixture for amplification of the second DNA strand where the amplification primers correspond to the adaptor sequence in the first strand generation primers and the second strand generation primer, respectively. Amplification products after the PCR amplification of the second DNA strand can be collected from the liquid phase of the reaction product.

The followings are some of the advantages of using the present method to generate library preparation for sequencing:

(1) In the first strand generation, the first strand is generated from total nucleic acid using a melt protocol which enables binding of the random sequence to both DNA and RNA molecules. Using a specific reverse transcriptase and adaptor sequence in the first strand generation primers to generate the first DNA strand allows a one-pot synthesis of the first strand DNA template from a mixture of different nucleic acids so to avoid bias;

(2) In the second strand generation, the second strand generation primer contains a random sequence to avoid concatemer formation during the second strand generation from the first DNA strand. Since the first DNA strand contains the adaptor sequence, the complementary adaptor sequence in the second strand generation primer results in a product that has a unique identifier on either end of the second DNA strand;

(3) Inclusion of a methylated dCT into the amplification primers which contain both the adaptor sequences of the first and second strand generation primers and addition of deoxy-methylated cytosine triphosphate into the PCR reaction mixture allows the subsequent restriction enzymatic digestion specific to those amplicons at the methylated base in order to reduce the size of the fragments under 1000 nucleotide;

(4) Appending adaptor sequence with 4 nt 5' overhangs allows later ligation of adaptors on both ends of the DNA fragments for subsequent sequencing PCR and barcoding.

BRIEF DESCRIPTION OF THE DRAWINGS

Embodiments of the invention are described in more details hereinafter with reference to the drawings, in which.

DEFINITION

"One-pot" described herein may refer to a single step of using a set of primers to prime DNA and at the same time prime RNA such as mRNA (e.g., by a primer with oligo-dT sequence at the 5' end of the two random nucleotides), with a polymerase with both DNA extension and RNA transcription abilities under suitable reverse transcription conditions so it can generate cDNA strand from both DNA and RNA templates, or any other oligonucleotide synthesis without additional purification and/or other methods to isolate one type of nucleic acid from the others because of the limitation of the oligonucleotide synthesis scheme provided by conventional technologies.

DETAILED DESCRIPTION OF THE INVENTION

In the following description, a simultaneous amplification method for generating a library from a mix of different nucleic acids without bias is set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

EXAMPLES

Example 1—Library Preparation from HEK293 Cells 10 ng or 1 ng of DNAse I-treated RNA harvested from HEK293 cells was mixed with 500 nM of adaptor A-B6

Figure 1:
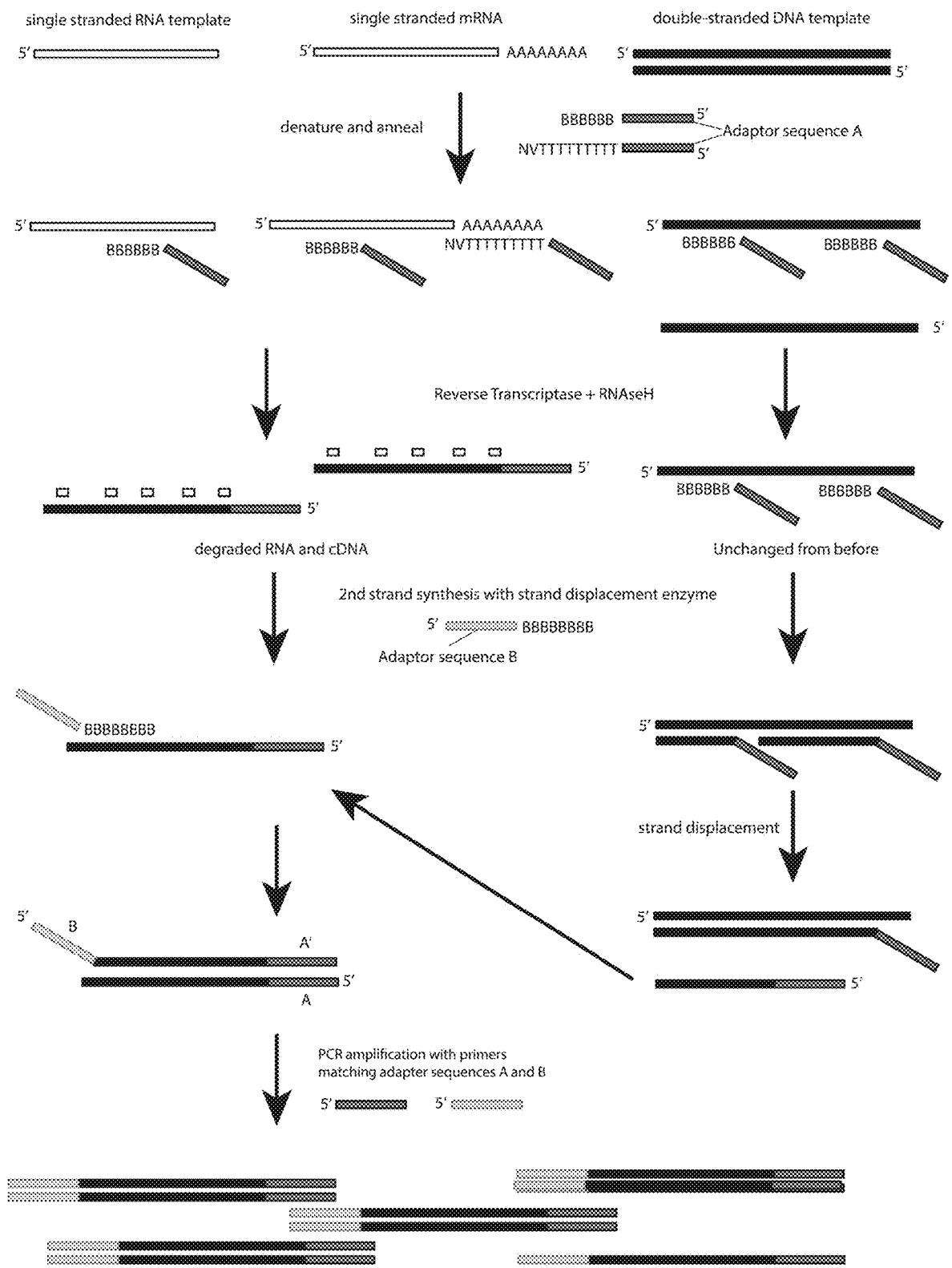
FIG. 1 schematically illustrates an embodiment of the present method to generate double-stranded DNA molecules from different nucleic acids using the first strand generation primers, second strand generation primers and corresponding amplification primers of the present invention.
Figure 2:
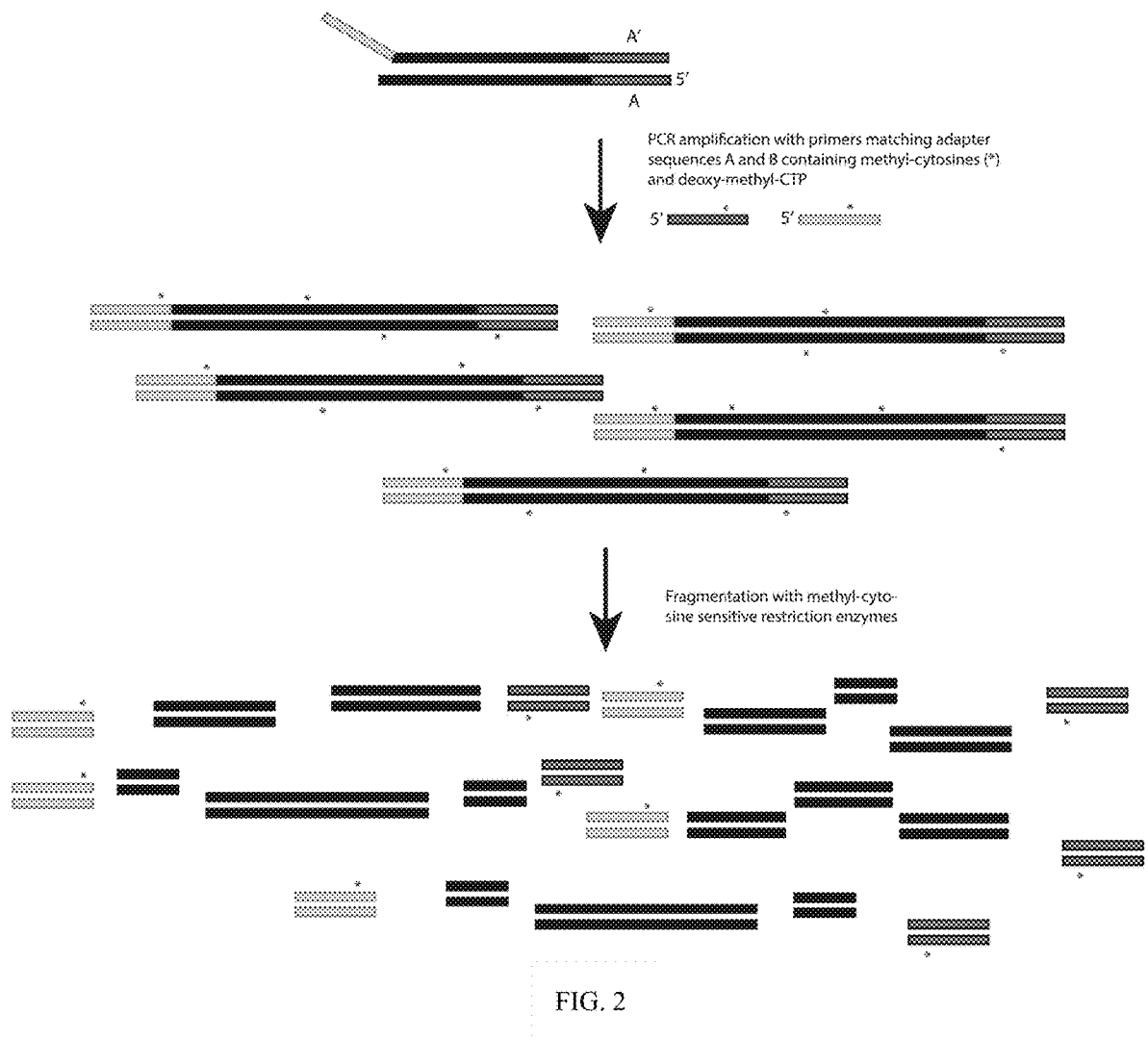
FIG. 2 schematically illustrates an embodiment of the present method to modify and fragment the double-stranded DNA molecules obtained from amplification of the second DNA strand as shown in FIG. 1 to generate double-strand DNA molecules with a linear length of shorter than 1000 nucleotides.
Figure 3:
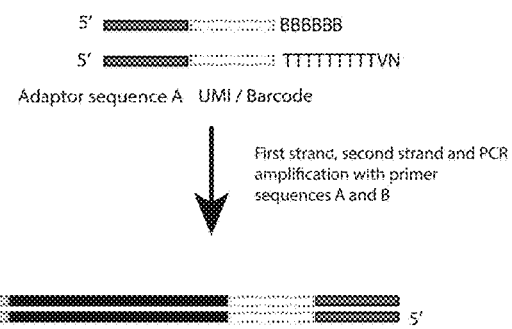
FIG. 3 schematically illustrates an embodiment of the present method to append corresponding adaptor sequences to the fragmented double-stranded DNA molecules as shown in FIG. 2 for barcoding.
Figure 4:
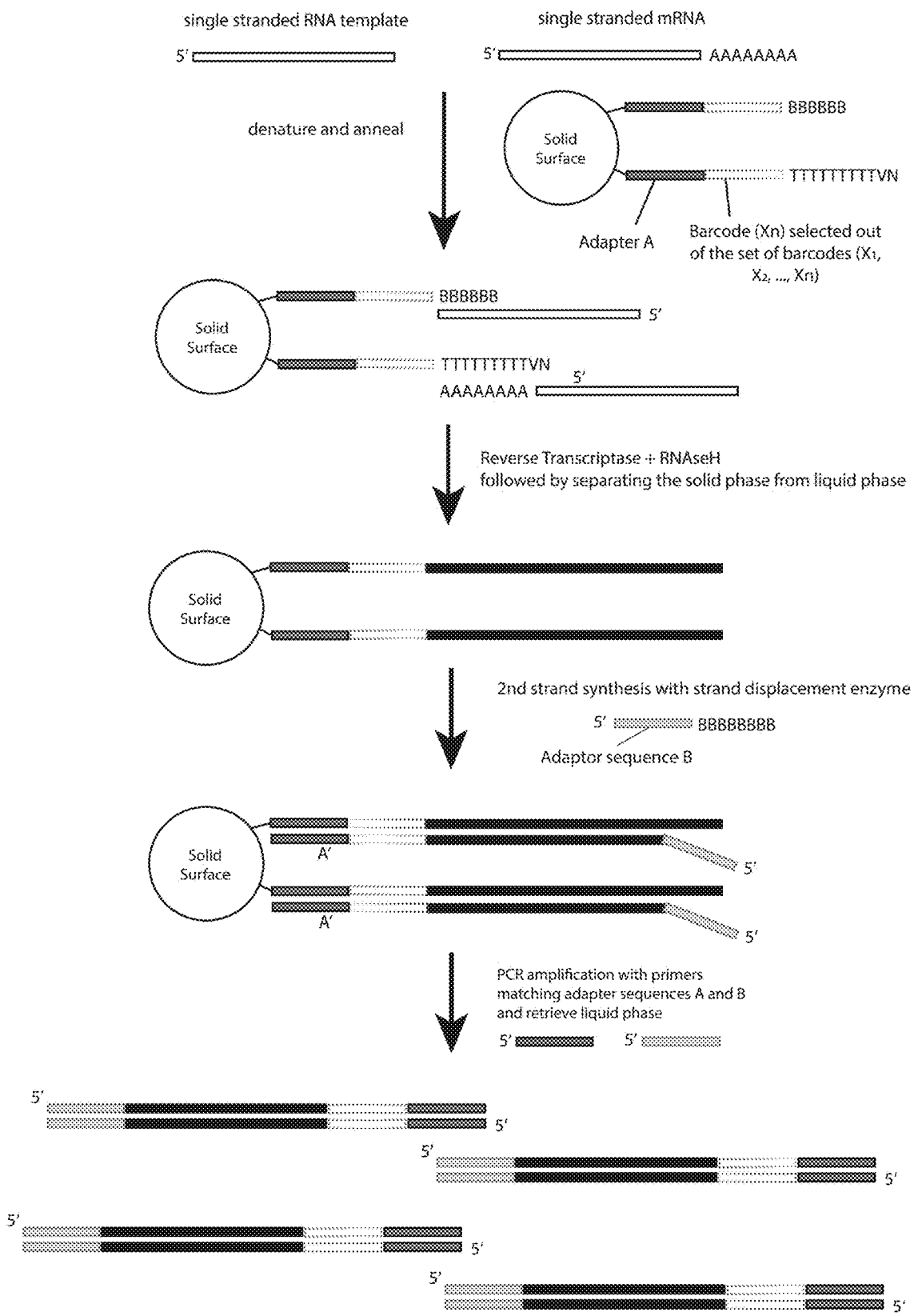
FIG. 4 schematically illustrates an embodiment of the present invention to prepare library from a sample with RNA template according to the present method and components described herein.

(5'-CAGACTACCATGACCTGAGTCBBBBBB-3') (SEQ ID NO: 1) and adaptor A-oligodT (5'-CAGACTAC-CATGACCTGAGTCTTTTTTTTTTTTTTTVN-3') (SEQ ID NO: 2) in a 1:1 ratio or adaptor A-oligodT alone in a 10 µl reverse transcription reaction mix using PROMEGA MMLV reverse transcriptase as per manufacturer's instructions at 40° C. for 15 minutes before denaturing at 70° C. for 5 minutes. 5 µl was stored for qPCR. 1 µl of 10 µM Adaptor B-B8 (5'-GTCAGAGTCGAATGCGTACTGBBBBBBBB-3') (SEQ ID NO: 3) was added to the other 5 µl of the RT reaction mix and heated to 70° C. for 2 minutes before cooling to 4° C. in the thermocycler. 1.5 µl Isothermal Buffer, 1.0 µl mM MgSO$_4$, 2.0 µl 2 mM dNTPs, 3.5 µl water and 1 µl Bst3.0 were then added and incubated in the thermocycler at 45° C. for 20 s, increasing 1° C. every 20 s to 60° C. and held at 60° C. for 12 minutes. 2.25 µl 10 µM of methylated Adaptor A primer (5'-CAGACTACm-CATGACCTGAGTC-3') (SEQ ID NO: 4) and methylated Adaptor B primer (5'GTCAGAGTmCGAATGCGTACTG-3') (SEQ ID NO: 5), 4.5 µl 2 mM dNTPs, 0.9 µl 1 µM dmCTP, 3.6 µl KOD buffer, 2.25 µl 25 mM MgSO4, 0.45 µl KOD was added and topped up with water to 45 µl. The template was then heated to 95° C. for 2 minutes, then cycled between 95° C. for 10 s, 58° C. for 10 s, 70° C. for 2 minutes for 10 cycles. The resultant 50 µl reaction mixture was then cleaned up with 1.0× Ampure XP beads as per manufacturer's instructions and eluted in 10 µl (FIG. 4).

Example 2—qPCR for Normalization of Input RNA

Figure 5A:
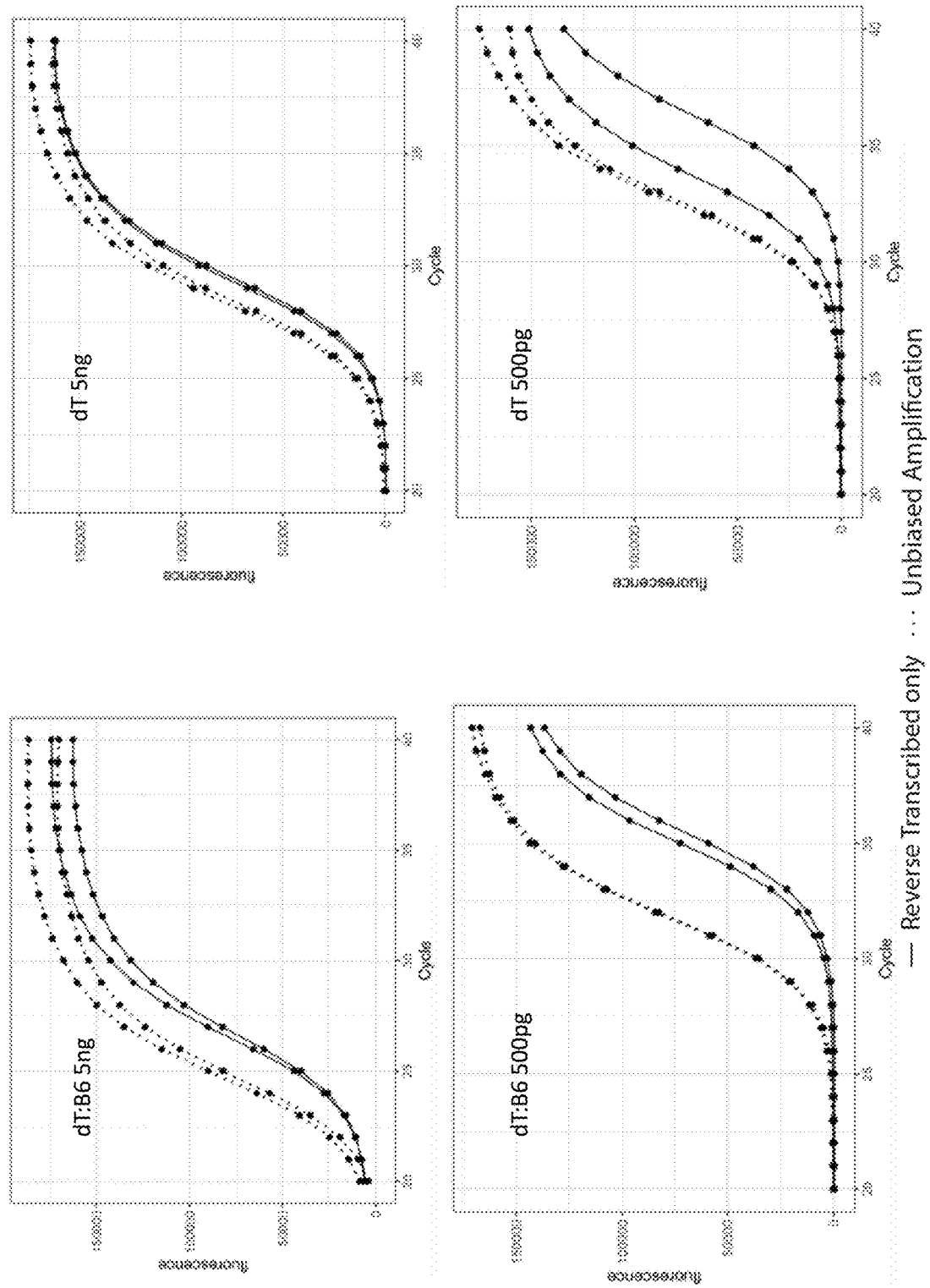
FIGS. 5A-5D illustrate the results of normalization of input RNA by qPCR using primers against human 18S (FIG. 5A), U2AF1 (FIG. 5B), GAPDH coding region (FIG. 5C) and GAPDH 3'UTR (FIG. 5D) from 5 ng/500 pg HEK293 cell RNA (dT 5 ng/500 pg) and the cleaned library preparation prepared using 5 ng/500 pg dT-adaptor B6 sequence (dT:B6 5 g/500 pg) according to Example 1.
Figure 5B:
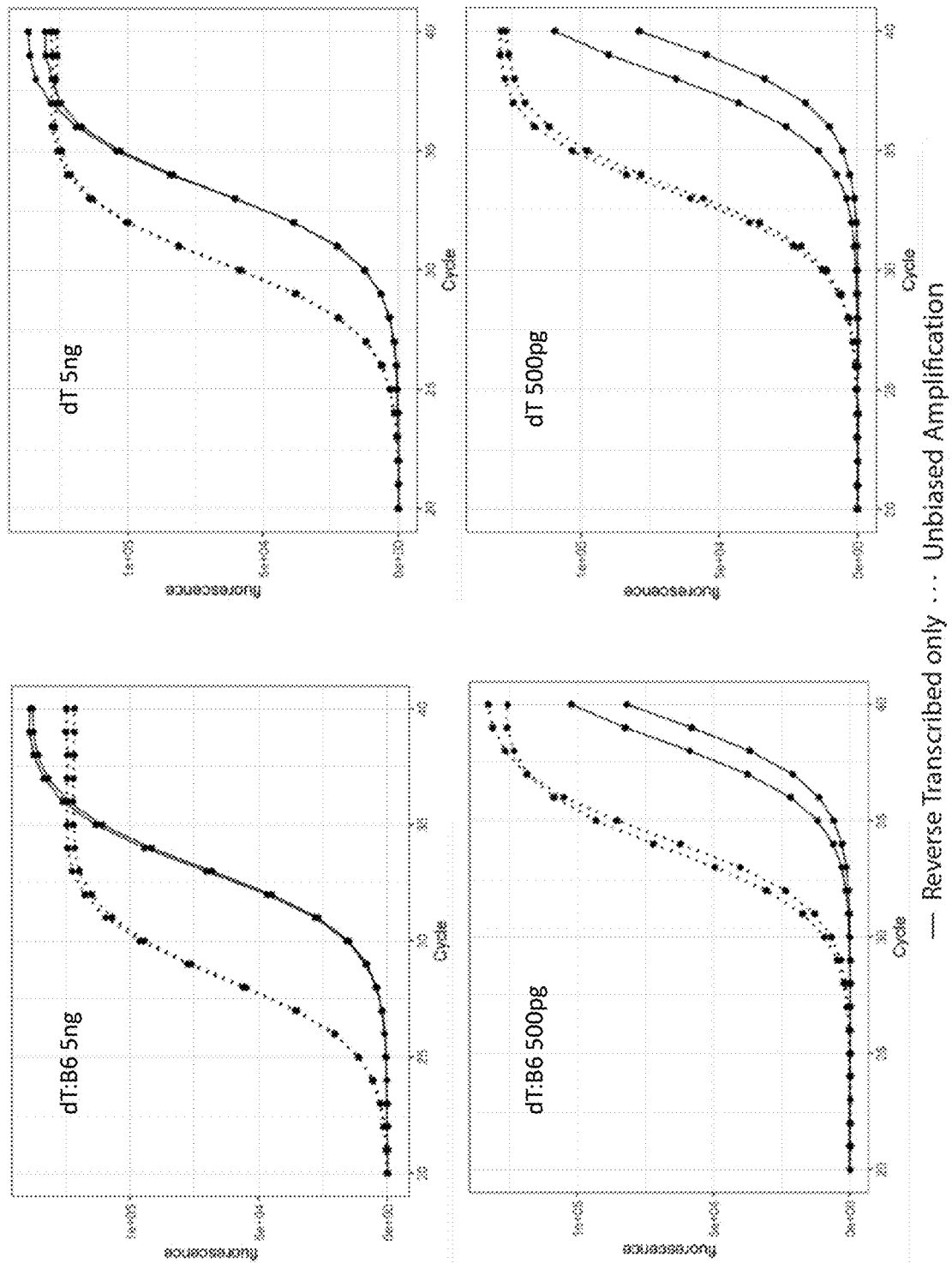
Figure 5C:
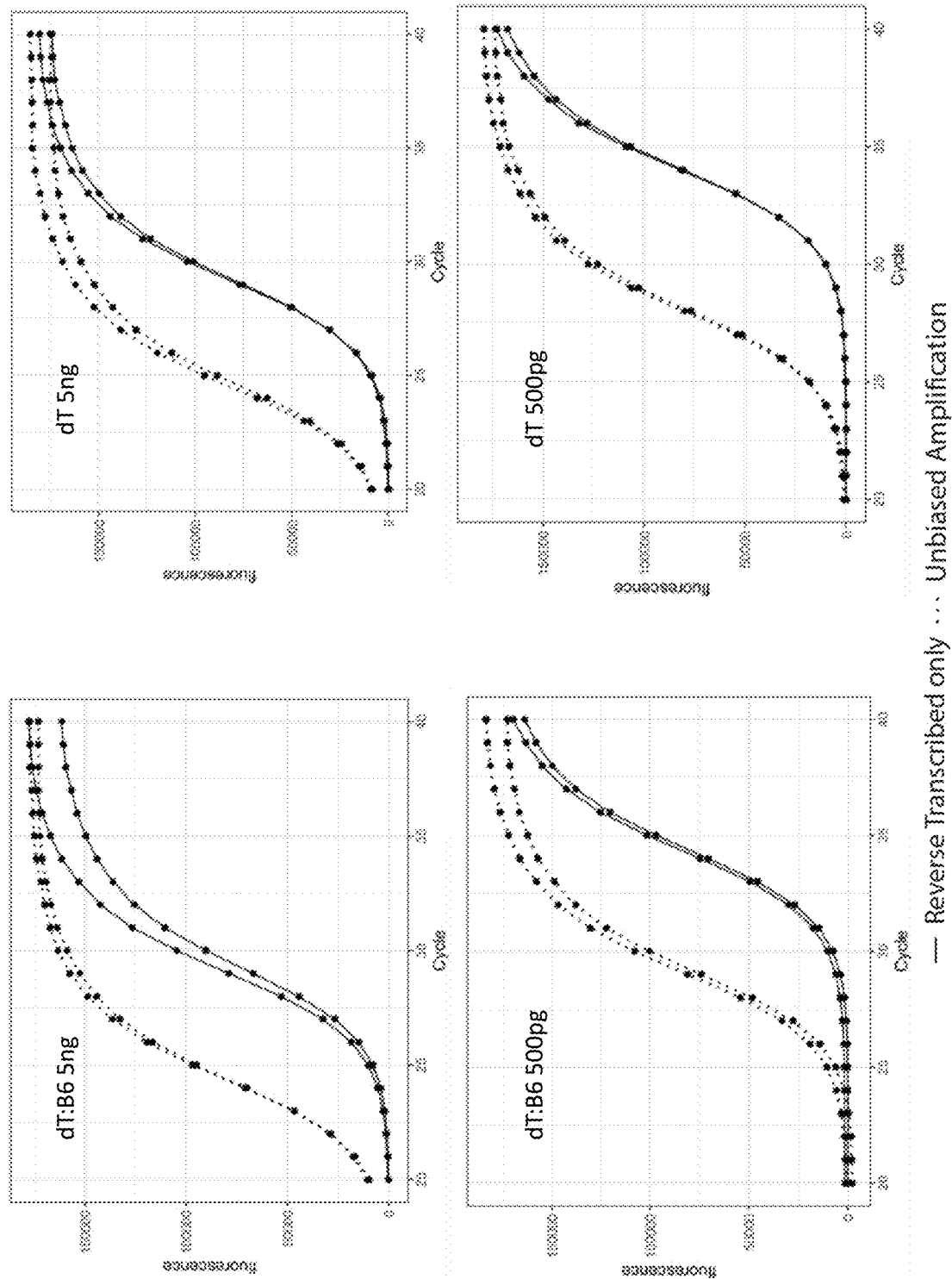
Figure 5D:
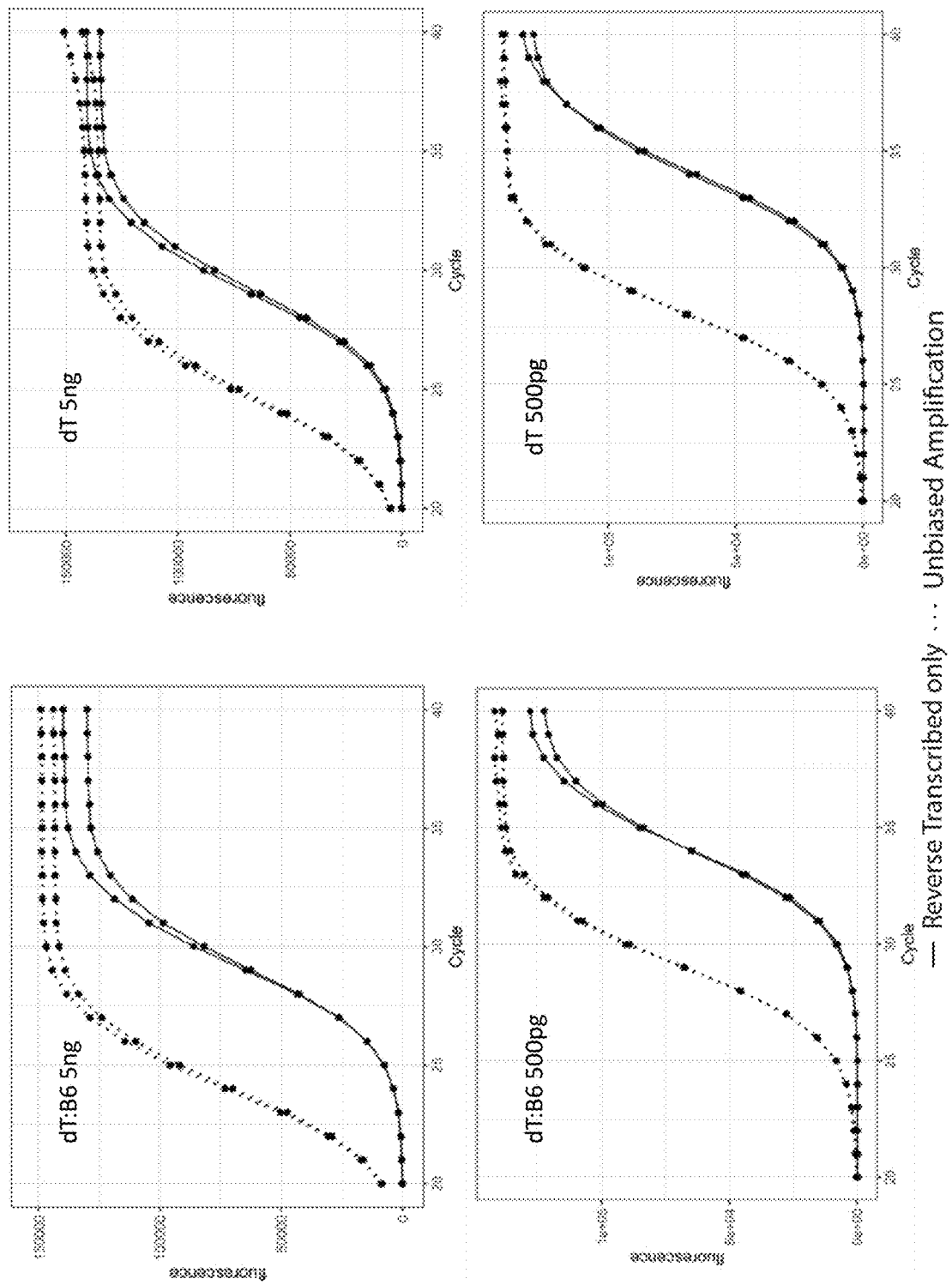

5 µl of RT is equivalent to 5 ng/500 µg of HEK293 RNA input and 10 µl of the Ampure XP cleaned library preparation is equivalent to the same input. The RT reaction mix saved from Example 1 was diluted 1:20 and the library prep was diluted 1:10, where 1 µl was used for each qPCR. qPCR was then performed using primers against human 18S (FIG. 5A), U2AF1 (FIG. 5B), GAPDH coding region (FIG. 5C) and GAPDH 3'UTR (FIG. 5D). After amplification according to the method described herein, all amplicons were demonstrated to be amplified using the unbiased amplification method described herein.

Example 3—DNA Fragmentation and Library Preparation

3 µl of the Ampure XP purified library from Example 1 was then digested by MspJI in a 5 µl reaction as per manufacturer's instructions for 15 minutes at 37° C. to fragment the library. 1.5 µl of double stranded adaptors, one of them is represented by (5'-AGATGTGTATAAGA-GACAG-3') (SEQ ID NO: 6) and the other with 4 nt 5' overhangs is represented by (5'-NNNNCTGTCTCTTATA-CACATCT-3') (SEQ ID No: 7), 7 µl of 2× Quick Ligase Buffer (NEB), 0.5 µl 2 mM dNTPs, 0.3 µl Recombinant Taq and 0.7 µl of Quick ligase were then added to ligate adaptors to the ends. This was then amplified with two primers (5'-TCGTCGGCAGCGTCAGATGTGTATAAGA-GACAG-3') (SEQ ID NO: 8) and 5'-GTCTCGTGGGCTCGGAGATGTGTATAAGA-GACAG-3') (SEQ ID NO: 9) in a KOD reaction for 10 cycles with 60° C. annealing temperature with 40 second elongation. The reaction was then barcoded using ILLUMINA barcoding primers and sequenced on an iSeq 100 as per manufacturer's protocol.

The followings are examples providing thermocycler setting and conditions (in Tables 3-10) used to generate the library from the reagents according to Tables 1 and 2:
1) Add up to 3 µl of sample nucleic acid to 1 µl of primers represented by SEQ ID NOs: 1-2, reaction mix of nucleotides and water and further top up to 4 µl with nuclease-free water if required. Put in thermocycler with the following setting (Table 1).

TABLE 1

| Thermocycler settings | |
|---|---|
| Temperature (° C.) | Time (mins:secs) |
| 70° C. | 1:00 |
| 4° C. | hold |

2) Add 1 µl of a reverse transcriptase (from NEB) and put in thermocycler with the following setting (Table 2).

TABLE 2

| Thermocycler settings | |
|---|---|
| Temperature (° C.) | Time (mins:secs) |
| 40° C. | 15:00 |
| 70° C. | 3:00 |
| 4° C. | hold |

3) Add 4 µl of primer represented by SEQ ID NO: 3 and a reaction mix including an isothermal buffer, oligonucleotides and water, and 1 µl of a polymerase with strand displacement activity on ice to bring the sample to a total of 10 µl and put in thermocycler with the following setting (Table 3).

TABLE 3

| Thermocycler settings | |
|---|---|
| Temperature (° C.) | Time (mins:secs) |
| 70° C. | 0:10 |
| 4° C. | 0:10 |
| 45° C. | 1:00 |
| 48° C. | 1:00 |
| 51° C. | 1:00 |
| 54° C. | 1:00 |
| 57° C. | 1:00 |
| 60° C. | 10:00 |
| 25° C. | hold |

4) Add 15 µl of reagents from KOD kit and a pair of amplification primers represented by SEQ ID NOs: 4 and 5, respectively, wherein cytosine at 9$^{th}$ position from 5'end of each of the amplification primers is methylated, and put in thermocycler with the following setting (Table 4).

TABLE 4

| Thermocycler settings | | |
|---|---|---|
| Temperature (° C.) | Time (mins:secs) | No. of cycles |
| 95° C. | 2:00 | |
| 95° C. | 0:08 | 15× |
| 58° C. | 0:10 | |
| 70° C. | 2:00 | |
| 25° C. | hold | |

5) Add 25 µl of Ampure XP (diluted) beads that has been brought up to room temperature and mix at least 10 times up and down with a pipette and let the sample incubate with the beads at room temperature for at least 3 minutes.

6) Use a magnetic rack to pull out the beads. Leave on rack for at least 2 minutes.

7) Remove supernatant, and resuspend the beads in 100 µl of freshly prepared 80% ethanol. Leave on magnetic rack for 20 seconds to pull out the beads. Repeat this step once more.

8) Remove supernatant and allow the beads to dry in room temperature for 5 minutes, then resuspend well in 8 µl of nuclease-free water. Incubate for 1 minute at room temperature before putting on the magnetic rack.

9) Carefully remove the eluate and transfer to a new tube.

10) Take 4 µl of the eluate and add 1 µl of reagents from MspJI kit in a new tube and put in thermocycler with the following setting (Table 5).

TABLE 5

| Thermocycler settings | |
| --- | --- |
| Temperature (° C.) | Time (mins:secs) |
| 37° C. | 12:00 |
| 70° C. | 5:00 |
| 4° C. | Hold |

11) Add 10 µl of reagents from Quick Ligase and Taq kits with primers represented by SEQ ID NOs. 6 and 7, respectively, to the sample to give a total of 15 µl and put in thermocycler with the following setting (Table 6).

TABLE 6

| Thermocycler settings | |
| --- | --- |
| Temperature (° C.) | Time (mins:secs) |
| 25° C. | 15:00 |
| 70° C. | 5:00 |
| 25° C. | Hold |

12) Add 25 µl of reagents from KOD kit with primer represented by SEQ ID NOs.: 8-9, respectively, to the sample to give a total of 40 µl and put in thermocycler with the following setting (Table 7).

TABLE 7

| Thermocycler settings | | |
| --- | --- | --- |
| Temperature (° C.) | Time (mins:secs) | No. of cycles |
| 95° C. | 2:00 | |
| 95° C. | 0:08 | 13× |
| 60° C. | 0:10 | |
| 70° C. | 0:40 | |
| 25° C. | hold | |

13) Take 5 µl of the sample from step 12, add 0.8 µl of each barcoding primer and 13.4 µl of the same reagents from KOD kit as in step 12 to give a total of 20 µl and put in thermocycler with the following setting (Table 8).

TABLE 8

| Thermocycler settings | | |
| --- | --- | --- |
| Temperature (° C.) | Time (mins:secs) | No. of cycles |
| 95° C. | 2:00 | |
| 95° C. | 0:08 | 7× |
| 55° C. | 0:10 | |
| 70° C. | 0:40 | |
| 25° C. | hold | |

14) Add 20 µl of Ampure XP (diluted) beads that has been brought up to room temperature and mix at least 10 times up and down with a pipette and let the sample incubate with the beads at room temperature for at least 3 minutes.

15) Use a magnetic rack to pull out the beads. Leave on rack for at least 2 minutes.

16) Remove supernatant, and resuspend the beads in 100 µl of freshly prepared 80% ethanol. Leave on magnetic rack for 20 seconds to pull out the beads. Repeat this step once more.

17) Remove supernatant and allow the beads to dry in room temperature for 5 minutes, then resuspend well in 8 µl of nuclease-free water. Incubate for 1 minute at room temperature before putting on the magnetic rack.

18) Carefully remove the eluate and transfer to a new tube.

19) The library is ready for sequencing.

N.B.: if the box in the column showing the number of cycles is blank, it may stand for 1 cycle.

Figure 6:
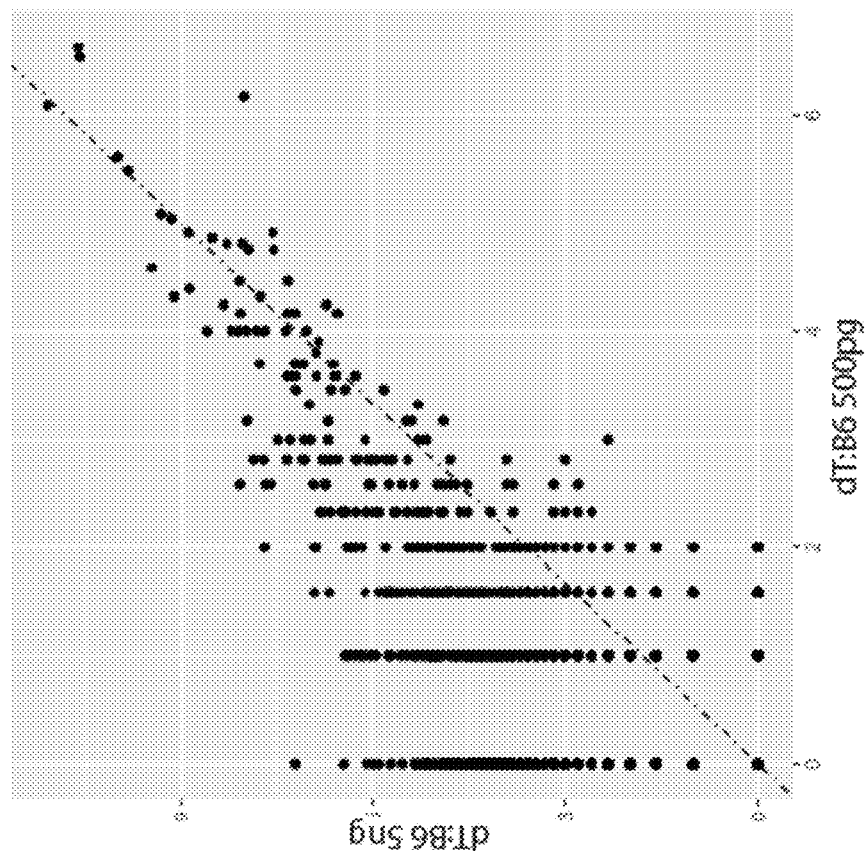
FIG. 6 illustrates two plots of the transcript reads between the samples using 5 ng of dT-adaptor B6 sequence (dT:B6 5 ng) and 5 ng of dT, and between dT:B6 5 ng and dT:B6 500 pg.
Figure 6:
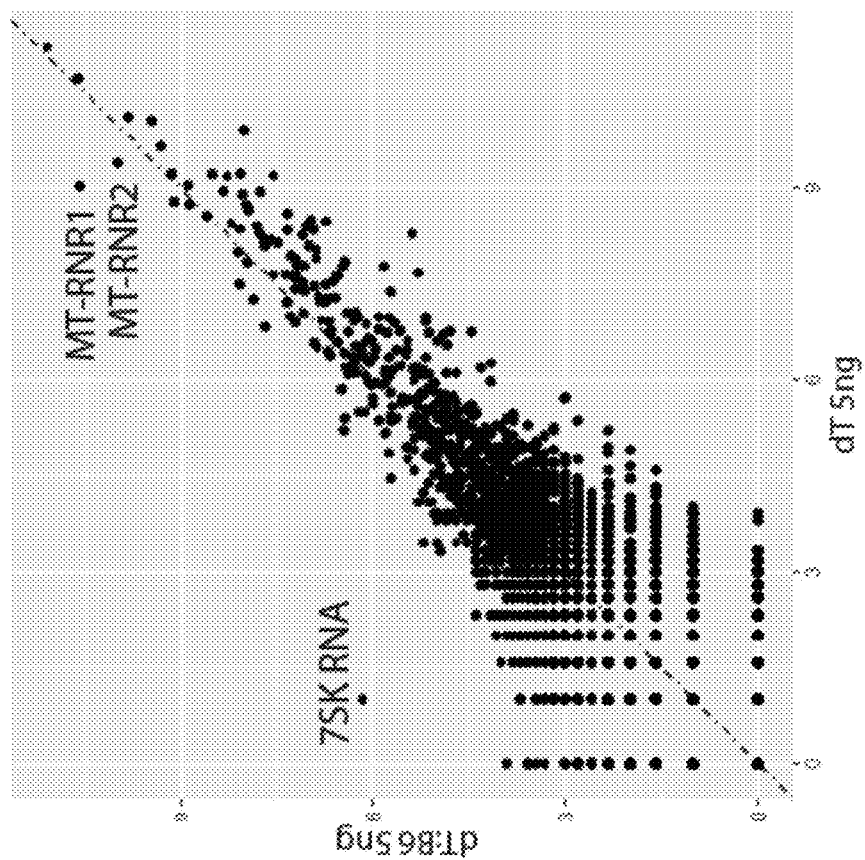

The results of the sequencing as shown in FIG. 6 and in Table 9 suggest that the library prepared according to the present method could detect over 9000 genes expressed in HEK cells with a read depth of between 60000-90000 reads.

TABLE 9

| | dT_B6_5ng | dT_5ng |
| --- | --- | --- |
| Total Reads | 63858 | 84849 |
| Number of transcripts mapped | 9410 | 12266 |

Furthermore, the read distributions of the dT_5 ng and dT_B6_5 ng samples are very similar, except the transcripts without a polyA tail, such as 7SK, mt-RNR1 and mt-RNR2. These results suggest that the present method generates an unbiased representative library.

Example 4—Comparison Between N, B, D, H and NTC in Terms of Background Amplification To identify potential background amplification, 0.4 µl of 5 µM of any one of N6 (CAGACTACCATGACCTGAGTC) (SEQ ID NO: 10), B6 (CAGACTACCATGACCT-GAGTCBBBBBB) (SEQ ID NO: 1), D6 (CAGACTAC-CATGACCTGAGTCDDDDDD) (SEQ ID NO: 11) or H6 (CAGACTACCATGACCTGAGTCHHHHHH) (SEQ ID NO: 12) was mixed with 0.2 µl of 25 mM dNTPs, 1.0 µl of 5×PROMEGA MMLV reverse transcriptase buffer and 3.1 µl of water, heated to 70° C. for 30 seconds and cooled to 4° C. Then 0.5 µl of PROMEGA MMLV reverse transcriptase was added and the reactions incubated at 40° C. for 15 minutes, followed by 70° C. for 5 minutes.

1.5 µl NEB Isothermal Buffer, 0.75 µl 25 mM MgSO4, 1.5 µl 2 mM dNTP, 0.5 µl Bst3.0, 4.8 µl water and 1.0 µl of N8 (GTCAGAGTCGAATGCGTACTG) (SEQ ID NO: 13), B8 (GTCAGAGTCGAATGCGTACTGBBBBBBBB) (SEQ ID NO: 3), D8 (GTCAGAGTCGAATGCGTACTGDDDDDDDD) (SEQ ID NO: 14) or H6 (GTCAGAGTCGAATGCGTACTGHHHHHHHH) (SEQ ID NO: 15) was added to the respective sample tubes as described above.

The samples were incubated at 45° C. for 20 s, increasing in steps of 1° C. every 20 s until the samples reaches 60° C. The samples were further incubated at 60° C. for 10 mins.

The resultant sample are diluted 1/100 and 1 µl put in a 20 µl qPCR reaction using Solis Biodyne's FIREPOL SyBr Green qPCR mastermix as per manufacturer's instruction and the following primers (GTCAGAGTCGAATGCGTACTG) (SEQ ID NO: 17) and (CAGACTACCATGACCTGAGTC) (SEQ ID NO: 18), cycling with the following protocol: 95° C. 15 s, 60° C. 15 s, 72° C. 40 s for 50 cycles.

The resultant qPCR Ct (Table 10) reveals the background level of an 'empty' reaction using different sets of random hexamers and octamers. With N, a low Ct indicates that background signal is significantly higher than with B, D or H set of bases.

Therefore, repeating B, D, or H of random hexamer or octamer at 3' end in the adaptor sequence of the first and second DNA strand generation primers reduce the chance of non-specific priming over the repeating N in the same region of the strand generation primers.

TABLE 10

| Sample | N6 + N8 | B6 + B8 | D6 + D8 | H6 + H8 | NTC |
|---|---|---|---|---|---|
| Replicate 1 | 14.9 | 15.44 | 18.76 | 20.91 | 31.33 |
| Replicate 2 | 14.89 | 15.38 | 17.93 | 20.92 | 26.15 |

Example 5

The following examples illustrates how DNA library is prepared according to other embodiments of the present invention:

1. To make 5 µM B5Y1: dT, mix 9.5 µl of 100 µM B5Y1 (represented by SEQ ID NO: 1) and 0.5 µl dT (represented by SEQ ID NO: 2) with 190 µl water;
2. To use 100 µM B7Y1 (represented by SEQ ID NO: 3) as it comes in from the oligonucleotide manufacturer;
3. To mix 3 µl 100 µM mC F (represented by SEQ ID NO: 4, wherein the cytosine at the 9$^{th}$ nucleotide from the 5' end is methylated), 3 µl 100 µM mC R (represented by SEQ ID NO: 5, wherein the cytosine at the 9$^{th}$ nucleotide from the 5' end is methylated), 1 µl 10 mM dmCTP (NEB) and 23 µl water;
4. To mix 3 µl 100 µM Adaptor F (represented by SEQ ID NO: 6), 3 µl 100 µM Adaptor R (represented by SEQ ID NO: 7), 3 µl 1 M sodium chloride, 3 µl 10×TE buffer, 18 µl water. Heat to 95° C. and cool down to 4° C. at 0.25° C. per second, to make 10 µm Adaptor mix;
5. To mix 15 µl 100 µM i5 F (represented by SEQ ID NO: 8), 15 µl 100 µM i7 R (represented by SEQ ID NO: 9) to make 50 µM i5 i7 Amp.

15 µl tubes are prepared with different primers ready for barcoding in a separate box.

Example 6—Functional Quality Control (QC) of DNA Library Preparation 5 ng of HEK293 in 3 µl is processed with the AmpRE kit, then run on gel or TapeStation. 200-500 nt smear should be seen.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

The invention claimed is:

1. An unbiased and simultaneous amplification method for preparing a library from a sample of more than one type of nucleic acid in substantially low amount comparative to non-nucleic acid molecules, where the method includes:
   providing the sample of more than one type of nucleic acid including single-stranded and/or double-stranded DNA and/or RNA as a template of subsequent extensions and amplifications;
   preparing a first DNA strand from said sample including annealing first DNA strand generation primers to any of the DNA and/or RNA template, and extending from the annealed first DNA strand generation primer including employing a DNA polymerase that enables a one-pot synthesis of the first DNA strand from either or both of DNA and/or RNA templates to obtain the first DNA strand, wherein the first DNA strand generation primers include:
      a first nucleotide sequence that includes a first adaptor sequence on the 5' end followed by a poly-thymidine sequence and two random nucleotides, said polythymidine sequence including at least ten thymidine bases followed by a random nucleotide V and further followed by a random nucleotide N, wherein V and N are according to IUPAC nucleotide code, and
      a second nucleotide sequence that includes the first adaptor sequence on the 5' end followed by six repeating random nucleotides, each of said six repeating random nucleotides being jointly or independently selected from B, D, H, or V according to IUPAC nucleotide code,
   preparing a second strand of DNA or DNA fragment including annealing a second DNA strand generation primer to the first DNA strand after dissociation from the DNA and/or RNA template and denaturing thereof, and extending from the annealed second DNA strand generation primer including employing a DNA polymerase having strand displacement activity, wherein said second DNA strand generation primer includes:
      a random nucleotide sequence including a plurality of random nucleotides at 3'-end, and
      a second adaptor sequence at 5'-end thereof that is physically linked to the random nucleotide sequence, wherein said plurality of random nucleotides includes eight repeating random nucleotides wherein each of said eight repeating random nucleotides is jointly or independently selected from B, D, H, or V according to IUPAC nucleotide code;
   amplifying the second strand of DNA or DNA fragment via a polymerase chain reaction including annealing a pair of amplification primers including the first adaptor sequence at 5'-end in one of the amplification primers and the second adaptor sequence at 5'-end in another one of the amplification primers to the second strand of DNA or DNA fragment to obtain a plurality of amplicons such that each of the amplicons includes at least the first and second adaptor sequences, wherein each of the first and second adaptor sequences has at least one nucleotide modified by methylation; and
   fragmenting the amplicons into a plurality of double-stranded DNA fragments including reacting the amplicons with a methylation-specific restriction enzyme in order to obtain the double-stranded DNA fragments absent the first and second adaptor sequences.

2. The method of claim 1, wherein one of the first DNA strand generation primers is represented by SEQ ID NO: 1.

3. The method of claim 1, wherein one of the first DNA strand generation primer is represented by SEQ ID NO: 2.

4. The method of claim 1, wherein the second DNA strand generation primer is represented by SEQ ID NO: 3.

5. The method of claim 1, wherein the first adaptor sequence is represented by SEQ ID NO: 4.

6. The method of claim 1, wherein the second adaptor sequence is represented by SEQ ID NO: 5.

7. The method of claim 1, wherein a methylated nucleoside triphosphate is added into a reaction mixture of the first and/or second DNA strand or DNA fragment preparation(s) and/or the polymerase chain reaction.

8. The method of claim 7, wherein the methylated nucleoside triphosphate is deoxy-methyl-cytidine triphosphate in a concentration of 0.01% to 25% to result in 0.01% to 25% of methylated cytosine in overall of the amplicons after the polymerase chain reaction.

9. The method of claim 5, wherein one cytosine in the first adaptor sequence is modified by methylation to become methyl-cytosine in order to obtain a plurality of amplicons with methylated nucleotide bases.

10. The method of claim 6, wherein one cytosine in the second adaptor sequence is modified by methylation to become methyl-cytosine in order to obtain a plurality of amplicons with methylated nucleotide bases.

11. The method of claim 1, wherein the first DNA strand generation primers are two different primers including the random nucleotide sequence including the plurality of random nucleotides and the poly-thymidine sequence followed by two random nucleotides, respectively, in a ratio of 1:1.

12. The method of claim 1, further comprising appending at least a pair of double-stranded adaptors, wherein one strand thereof comprises a 4-random nucleotide overhang complementary to a 4-nucleotide overhang on both ends of the double-strand DNA fragments after said fragmenting in order to obtain double-stranded DNA fragments under 1000 nucleotide in size containing the double-stranded adaptors appended on both ends thereof.

13. The method of claim 12, further comprising appending a pair of sequencing adaptors on both ends of the double-stranded DNA fragments having been appended with the corresponding double-stranded adaptors, respectively, for subsequent barcoding.

* * * * *